United States Patent [19]
Singer

[11] 3,992,402
[45] Nov. 16, 1976

[54] HERBICIDAL AND/OR FUNGICIDAL 5-POLYHALOETHYLIMINO- AND 5-POLYHALOVINYLIMINO-2,4-IMIDAZOLIDINEDIONES

[75] Inventor: Malcolm S. Singer, Richmond, Calif.

[73] Assignee: Chevron Research Company, San Francisco, Calif.

[22] Filed: Aug. 29, 1975

[21] Appl. No.: 608,856

Related U.S. Application Data

[60] Division of Ser. No. 455,167, March 27, 1974, Pat. No. 3,925,553, which is a continuation-in-part of Ser. No. 239,357, March 29, 1972, Pat. No. 3,822,282.

[52] U.S. Cl. .............................................. 260/309.5
[51] Int. Cl.$^2$ ........................................ C07D 233/88
[58] Field of Search ................................... 260/309.5

[56] References Cited
FOREIGN PATENTS OR APPLICATIONS
2,013,098   3/1970   France ............................. 260/309.5

Primary Examiner—Natalie Trousof
Attorney, Agent, or Firm—G. F. Magdeburger; Dix A. Newell; Raymond Owyang

[57] ABSTRACT

5-(1-Hydroxy-2,2,2-trihaloethylimino)-, 5-(1,2,2,2-tetrahaloethylimino)- and 5-(polyhalovinylethylimino)-2,4-imidazolidinediones and their use as herbicides and fungicides.

7 Claims, No Drawings

HERBICIDAL AND/OR FUNGICIDAL 5-POLYHALOETHYLIMINO- AND 5-POLYHALOVINYLIMINO-2,4-IMIDAZOLI-DINEDIONES

CROSS REFERENCE TO RELATED APPLICATIONS

This application is a division of application Ser. No. 455,167, filed Mar. 27, 1974, now U.S. Pat. No. 3,925,553, which is a continuation-in-part of copending application Ser. No. 239,357, filed Mar. 29, 1972, now U.S. Pat. No. 3,822,282, the disclosure of which is incorporated herein by reference.

BACKGROUND OF THE INVENTION

This invention relates to 5-imino-2,4-imidazolidinediones and their use as herbicides and fungicides.

Canadian Pat. No. 879,711, issued Aug. 31, 1971 to Malcolm S. Singer, common assignee, discloses herbicidal 5-imino-2,4-imidazolidinediones wherein the nitrogen in the 1 position of the imidazolidinedione nucleus is substituted with an aryl radical, the nitrogen in the 3 position is substituted with an aliphatic radical and the imino group is optionally substituted with a carbamoyl or N-chloroacetylcarbamoyl radical.

DESCRIPTION OF THE INVENTION

The imidazolidinediones of the invention are represented by the formula (I)

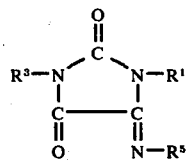

wherein $R^1$ and $R^3$ independently are alkyl of 1 to 6 carbon atoms, alkenyl of 3 to 6 carbon atoms, naphthyl, phenyl, phenyl substituted with from 1 to 4 halogens of atomic number 9 to 35 (fluorine, chlorine or bromine) or from 1 to 2 alkoxy groups of 1 to 4 carbon atoms, alkphenyl of from 7 to 12 carbon atoms, or alkphenyl of from 7 to 12 carbon atoms and substituted with from 1 to 4 halogens of atomic number 9 to 35 or from 1 to 2 alkoxy groups of 1 to 4 carbon atoms; and $R^5$ is 1-hydroxy-2,2,2-trihaloethyl, 1,2,2,2-tetrahaloethyl, trihalovinyl or dihalovinyl wherein the halogen is of atomic number 17 to 35 (chlorine or bromine).

Illustrative alkyl $R^1$ and $R^3$ groups are methyl, ethyl, isopropyl, n-propyl and n-butyl. Illustrative alkenyl $R^1$ and $R^3$ groups are allyl, 2-butenyl, and 3-pentenyl. Illustrative aromatic $R^1$ and $R^3$ groups are phenyl; alkphenyl groups such as tolyl, xylyl, p-ethylphenyl; and alkoxy- and halo-substituted phenyl and alkphenyl such as 2-flurophenyl, 2-chlorophenyl, 3-chlorophenyl, 3-fluorophenyl, 4-fluorophenyl, 4-chlorophenyl, 2,4-difluorophenyl, 3,4-difluorophenyl, 2,4-dichlorophenyl, 3-bromophenyl, 3,5-difluorophenyl, 3,5-dichlorophenyl, 2-fluoro-4-methylphenyl, 2-methyl-4-chlorophenyl, 4-methoxyphenyl, 2,4-diethoxyphenyl, 2-butoxyphenyl, 2-propoxy-4-methylphenyl, 2-chloro-4-methoxyphenyl, 2-chloro-4-methoxyphenyl. Illustrative $R^5$ groups are 1-hydroxy-2,2,2-trichloroethyl, 1-hydroxy-2,2,2-tribromoethyl, 1-hydroxy-2-bromo-2,2-dichloroethyl, 1,2,2,2-tetrachloroethyl, 1,2,2,2-tetrabromoethyl, 1,2,2-trichloro-2-bromoethyl, trichlorovinyl, 1,2-dichloro-2-bromovinyl, tribromovinyl, 2,2-dichlorovinvl, 2,2-dibromovinyl.

Representative imidazolidinediones of formula (I) are:

1-methyl-3-(4-fluorophenyl)-5-(1,2,2,2-tetrachloroethylimino)-imidazolidine-2,4-dione,
1-ethyl-3-(2,4-difluorophenyl)-5-(1-hydroxy-2,2,2-trichloroethylimino)-imidazolidine-2,4-dione,
1-propyl-3-tolyl-5-(1-hydroxyl-2,2,2-tribromoethylimino)-imidazolidine-2,4-dione,
1-isopropyl-3-(3,5-dibromophenyl)-5-(1-hydroxy-2,2,2-trichloroethylimino)-imidazolidine-2,4-dione,
1-phenyl-3-methyl-5-(1,2,2,2-tetrabromoethylimino)-imidazolidine-2,4-dione,
1-(4-chlorophenyl)-3-ethyl-5-(1-bromo-2,2,2-trichloroethylimino)-imidazolidine-2,4-dione,
1-(2,4-dichlorophenyl)-3-propyl-5-(1,2,2,2-tetrachloroethylimino)-imidazolidine-2,4-dione,
1-(2,4-dichlorophenyl)-3-propyl-5-(1,2,2,2-tetrachloroethylimino)-imidazolidine-2,4-dione,
1-(3,5-dichlorophenyl)-3-n-butyl-5-(1,2,2,2-tetrachloroethylimino)-imidazolidine-2,4-dione,
1-methyl-3-(2-fluorophenyl)-5-(1,2,2,2-tetrachloroethylimino)-imidazolidine-2,4-dione,
1-methyl-3-(2-chlorophenyl)-5-(1-hydroxy-2,2,2-trichloroethylimino)-imidazolidine-2,4-dione,
1-methyl-3-phenyl-5-(1-hydroxy-2,2,2-trichloroethylimino)-imidazolidine-2,4-dione,
1-methyl-3-(2,4-difluorophenyl)-5-(1-hydroxy-2,2,2-trichloroethylimino)-imidazolidine-2,4-dione,
1-(2-fluorophenyl)-3-methyl-5-(1,2,2,2-tetrachloroethylimino)-imidazolidine-2,4-dione,
1-(2-chlorophenyl)-3-methyl-5-(1,2,2-trichloro-2-bromoethylimino)-imidazolidine-2,4-dione,
1-(2-bromophenyl)-3-methyl-5-(1-hydroxy-2,2-dichloro-2-bromoethylimino)-imidazolidine-2,4-dione,
1-(2,4-difluorophenyl)-3-methyl-5-(1,2,2,2-tetrachloroethylimino)-imidazolidine-2,4-dione,
1-(2-fluorophenyl)-3-methyl-5-(trichlorovinylimino)-imidazolidine- 2,4-dione,
1-(4-chlorophenyl)-3-methyl-5-(trichlorovinylimino)-imidazolidine-2,4-dione,
1-methyl-3-phenyl-5-(trichlorovinylimino)-imidazolidine-2,4-dione,
1-(3,4-dichlorophenyl)-3-methyl-5-(dichlorovinylimino)-imidazolidine-2,4-dione,
1-methyl-3-(3,5-difluorophenyl)-5-(trichlorovinylimino)-imidazolidine-2,4-dione,
1-methyl-3-(4-bromophenyl)-5-(dibromovinylimino)-imidazolidine-2,4-dione,
1-(4-methoxyphenyl)-3-methyl-5-(1,2-dichloro-2-bromovinylimino)-imidazolidine-2,4-dione,
1-methyl-3-(3-methoxyphenyl)-5-(1-bromo-2,2-dichlorovinylimino)-imidazolidine-2,4-dione.

Preferred compounds of formula (I) are those wherein one $R^1$ or $R^3$ group is alkenyl, naphthyl, phenyl, alkphenyl, alkoxy- or halo-substituted phenyl or alkphenyl and the other $R^1$ or $R^3$ group is alkyl, especially methyl. Particularly preferred compounds of formula (I) are those wherein one $R^1$ or $R^3$ is halo-substituted phenyl or alkphenyl of 1 to 2 halogens of atomic number 9 to 17 and the other $R^1$ or $R^3$ is methyl.

A class of compounds represented by formula (I) is that wherein one $R^1$ or $R^3$ group is alkyl of 1 to 6 carbon atoms and the other $R^1$ or $R^3$ group is alkenyl of 3 to 6 carbon atoms or naphthyl and $R^5$ is 1-hydroxy-2,2,2-trihaloethyl, 1,2,2,2-tetrahaloethyl trihalovinyl or dihalovinyl wherein the halopgen is of atomic number 17 to 35, especially when one $R^1$ or $R^3$ group is alkyl and the other $R^1$ or $R^3$ group is alkenyl.

The imidazolidinediones of the invention where $R^5$ is a 1-hydroxy-2,2,2-trihaloethyl group are prepared by reacting a 5-iminoimidazolidine-2,4-dione with a trihaloacetaldehyde according to the following equation (I):

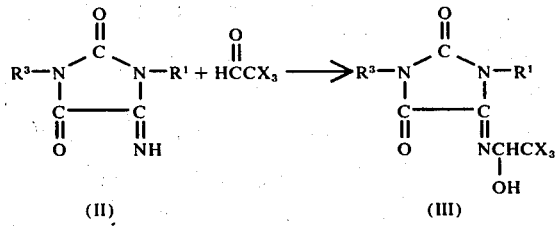
(1)

wherein $R^1$ and $R^3$ have the same significance as previously defined and X is chloro or bromo. It is appreciated, of course, that the OH-CHCX$_3$ group is the group $R^5$ of formula (I).

The 5-iminoimidazolidine-2,4-dione reactants (formula (II) are known compounds and are described in Canadian Pat. No. 879,711, issued Aug. 31, 1971, to M. S. Singer.

Suitable trihaloacetaldehyde reactants are trichloroacetaldehyde, dichlorobromoacetaldehyde and tribromoacetaldehyde.

The reaction depicted by equation (I) is conducted in an inert solvent or neat. Generally, stoichiometric amounts of imidazolidinedione and aldehyde are employed. The reaction is preferably catalyzed by a small amount of a strong inorganic acid, e.g., sulfuric or perchloric acid. The reaction temperature is generally in the range of about 20° to 100° C. The reaction proceeds rapidly and is generally complete in a matter of minutes. Reaction times of from 30 seconds to 10 hours are generally sufficient.

The imidazolidinediones of the invention wherein $R^5$ is a 1,2,2,2-tetrahaloethyl group are prepared by reacting the hydroxyimidazolidinedione (represented by formula (III) either in purified form or in the reaction mixture of equation (1) with a thionyl halide according to the following equation (2):

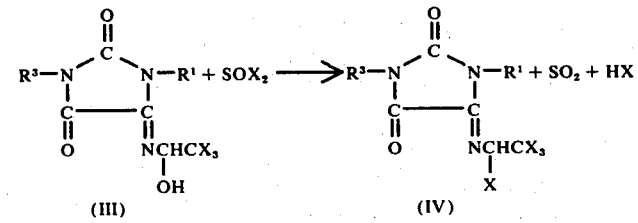
(2)

wherein $R^1$, $R^3$ and X have the same significance as previously defined.

The reaction depicted by equation (2) is accomplished by using from one mol to an excess of as much as 20 mols of the thionyl halide per mol of the imidazolidinedione reactant (III). The reaction temperature suitably varies from 20 to 100° C. and the reaction time suitably varies from 1 to 20 hours. If desired, the chloro- or bromoimidazolidinedione (IV) can be prepared directly from the 5-iminoimidazolidinedione reactant (II), the aldehyde reactant and the thionyl halide reactant in the same reactor by the general procedure employed for the reaction depicted by equation (2).

The compounds of the invention wherein $R^5$ is a 2,2-dihalovinyl or trihalovinyl group are prepared by dehalogenation or dehydrohalogenation of the tetrahaloethyl compound (IV), as depicted by reaction (3):

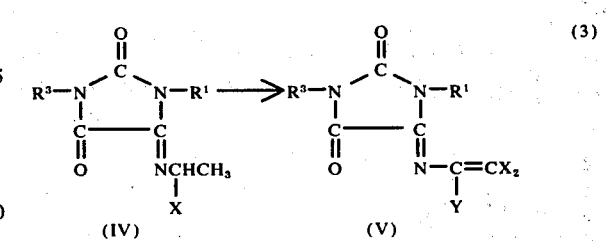
(3)

wherein $R^1$, $R^3$ and X have the same significance as previously defined, and Y is X or hydrogen. It is appreciated, of course, that Y is X when reaction (3) depicts a dehydrohalogenation reaction and that Y is hydrogen when equation (3) depicts a dehalogenation reaction. The dehydrohalogenation reaction is conducted under very mild basic conditions by conventional procedures at a temperature of from about 0° to 30° C. and for a reaction time of about 15 minutes to 2 hours. The dehalogenation reaction is conducted by reacting the tetrahaloethyl compound (IV) with zinc metal by conventional procedures, e.g., in inert solvent at 25° to 100° C.

The preparation of the compounds of the invention are further illustrated by the following examples:

EXAMPLES

EXAMPLE 1

Preparation of 1-phenyl-3-methyl-5-(1-hydroxy-1,2,2,2-tetrachloroethylimino)-imidazolidine-2,4-dione 1-phenyl-3-methyl-5-iminoimidazolidine-2,4-dione (15.0 g — 0.074 mol) was slurried in 40 ml chloroform. Chloral (21.8 g — 0.148 mol) was added directly to the slurry. Exothermicity raised the temperature 20° C. The reaction mixture was momentarily homogeneous before an abundance of product precipitated. An additional 100 ml of chloroform was added at this point. After 0.5 hour the mixture was filtered. The filter cake was washed with chloroform and dried. The product melted at 130°–133° C.

Elemental analysis showed: %C, calc. 41.1, found 41.8; %H, calc. 2.9, found 2.8; %N, calc. 12.0, found 12.3; %Cl, calc. 30.3, found 30.6.

EXAMPLE 2

Preparation of 1-(2-fluorophenyl)-3-methyl-5-(1,2,2,2-tetrachloroethylimino)-imidazolidine-2,4-dione 1-(2-fluorophenyl)-3-methyl-5-iminoimidazoladine-2,4-dione (10.0 g — 0.045 mol) was slurried in 80 ml of 1,2-dimethoxyethane. Chloral (13.4 g — 0.090 mol) was added, followed by the addition of 10.8 g (0.090 mol) thionyl chloride. The reaction mixture became homogeneous as the temperature rose from the heat of reaction. Temperature was maintained at 35°–45° C. for ½ hour. Solvent was removed from the mixture and the residue was taken up in benzene. Filtration removed some high-melting white solids. Hexane was added to precipitate the product, which was filtered and washed with ether. The product melted at 175°–177° C.

Elemental analysis showed: %C, calc. 37.2, found 37.5; %H, calc. 2.1, found 1.9; %N, calc. 10.9, found 10.9; %Cl, calc., 36.6, found 36.3.

EXAMPLE 3

Preparation of 1-(4-chlorophenyl)-3-methyl-5-(trichlorovinylimino)-imidazolidine-2,4-dione 1-(4-chlorophenyl)-3-methyl-5-(1,2,2,-tetrachloroethylimino)-imidazolidine-2,4-dione (10.0 g — 0.025 mol) was slurried in 35 ml acetonitrile. As triethylamine (2.5 — 0.025 mol) was added, the mixture became homogeneous and turned yellow. A precipitate began forming very soon after the triethylamine was added. Two hours later the mixture was filtered. The solid was a water-soluble amine hydrochloride. The filtrate was taken up in 75 ml methylene chloride, washed once with 75 ml water and dried over anhydrous magnesium sulfate. After filtration and solvent removal, the residual oil crystallized. It was stirred in ethanol and filtered to give 5.0 g of a yellow solid, m.p. 108°–110° C.

Elemental analysis showed: %C, calc. 39.27, found 40.6; %H, calc. 1.92, found 1.7; %N, calc. 11.45, found 11.7.

EXAMPLE 4

Preparation of 1-(2-fluorophenyl)-3-methyl-5-dichlorovinylimino)-imidazolidine-2,4-dione A mixture of 5 g (0.012 mol) -1(2-fluorophenyl)-3-methyl-5-(1-bromo-2,2,2-trichloroethylimino)-imidazolidine-2,4-dione and 1.6 g (0.024 mol) zinc powder in 15 ml dimethoxyethane was heated under reflux for 16 hours. The hot reaction mixture was filtered and the solvent removed by evaporation under reduced pressure. The residue was a yellow oil which cystallized from ethanol as a pale yellow powder, m.p. 135°–138° C.

Elemental analysis showed: %C, calc. 45.6, found 45.0; %H, calc. 2.6, found 2.2; %Cl, calc. 22.4, found 22.09, %N, calc. 13.29, found 13.4.

EXAMPLE 5

Preparation of 1-allyl-3-methyl-5-(trichlorovinylimino)-imidazolidine-2,4-dione 1-allyl-3-methyl-5-iminoimidazolidine-2,4-dione (20.0 g — 0.12 mol) and 17.7 g (0.12 mol) chloral in 50 ml chloroform were stirred at 25° C. for ½ hour. To the resulting solution was added 28.69 (0.24 mol) thionyl chloride. The temperature rose to 35° C. and a precipitate formed. The reaction mixture was heated at 55° C. for 2 hours, cooled and filtered. The filtrate was stripped to give 24 g of 1-allyl-3-methyl-5-(1,2,2,2-tetrachloroethylimino)-imidazolidine-2,4-dione, as a yellow oil.

A 7.3 g (0.072 mol) sample of triethylamine was added to a stirred mixture of 24 g 1-allyl-3-methyl-5-(1,2,2,2-tetrachloroethylimino)-imidazolidine-2,4-dione (prepared above) and 60 ml acetonitrile. A precipitate formed. The reaction mixture was stirred for 1½ hours and filtered. The filtrate was diluted with 60 ml methylene chloride, washed with water, dried over magnesium sulfate, and stripped to give the product as an orange oil. Thin-layer chromatography showed the product to be homogeneous.

Elemental analysis showed: %C, calc. 36.5, found 35.8; %H, 2.7, found 2.5; %Cl, calc. 35.9, found 35.5; %N, calc. 14.2, found 13.2.

Other compounds of the invention were prepared using the methods as described above. These compounds are tabulated in Table I.

UTILITY

The imidazolidinediones of the present invention are, in general, herbicidal in both pre- and post-emergent applications. For pre-emergent control of undesirable vegetation, these imidazolidinediones will be applied in herbicidal quantities to the environment, e.g., soil infested with seeds and/or seedlings of such vegetation. Such application will inhibit the growth of or kill the seeds, germinating seeds and seedlings. For post-emergent applications, the imidazolidinediones of the present invention will be applied directly to the foliage and other plant parts. Generally they are effective against weed grasses as well as broadleaved weeds. Some may be selective with respect to type of application and/or type of weed.

The imidazolidinediones of the invention are particularly effective as pre-emergent herbicides.

Pre-emergent herbicidal tests on representative imidazolidinediones of the invention were made using the following method:

EXAMPLE 6

Pre-emergent Herbicide Test

An acetone solution of the test imidazolidinedione was prepared by mixing 750 mg imidazolidinedione, 220 mg of a nonionic surfactant and 25 ml of acetone. This solution was added to approximately 125 ml of water containing 156 mg of surfactant.

Seeds of the test vegetation were planted in a pot of soil and the imidazolidinedione solution was sprayed uniformly onto the soil surface at a dose of 100 mcgm/c². The pot was watered and placed in a greenhouse. The pot was watered intermittently and was observed for seedling emergence, health of emerging seedlings, etc., for a 3-week period. At the end of this period, the herbicidal effectiveness of the imidazolidinedione was rated based on the physiological observations. A 0-to-100 scale was used, 0 representing no phytotoxicity and 100 representing complete kill. The results are reported in Table II.

when used as herbicides, the amount of imidazolidinedione administered will vary with the particular plant part or plant growth medium which is to be contacted, the general location of application — i.e., sheltered areas such as greenhouses as compared to exposed areas such as fields, as well as the desired type of control. For pre-emergent control of most plants, dosages in the range of about 0.5 to 20 lbs/acre will be used. Such administration will give a concentration of about 2 to 30 ppm imidazolidinedione distributed throughout 0.1 acre-foot. For post-emergent application, such as foliar spray application, compositions containing about 0.5 to 8 lbs. imidazolidinedione per 100 gal of spray will be used. Such application is equivalent to about 0.5 to 20 lbs imidazolidinedione per acre.

The herbicidal compositions of this invention comprise an herbicidal amount of one or more of the above-described imidazolidinediones intimately admixed with a biologically inert carrier. The carrier may be a liquid diluent such as water or acetone or a solid. The solid may be in the form of dust, powder or granules. These compositions will ususally also contain adjuvants such as a wetting or dispersing agent to facilitate their penetration into the plant growth medium or plant tissue and generally enhance their effectiveness. These compositions may also contain other pesticides, stabilizers, conditioners, fillers, and the like.

EXAMPLE 7

Fungus Spore Test 1-(2-fluorophenyl)-3-methyl-5-(1,2,2,2-trichlorovinylimino)-imidazolidine-2,4-dione and 1-phenyl-3-methyl-5-(1,2,2-trichlorovinylimino)-imidazolidine were tested for effectiveness against spores of Monilinia fructicola by means of a variation of "The Standard Spore Slide — Germination Method for Determining Fungicidal Activity," described in the "American Phytopathological Society Journal," Vol. 33, 627–632 (1943). The method measures the fungitoxic activity of fungicidal chemicals, their activity being expressed in terms of percent inhibition of germination of fungus spores. The compounds tested were dissolved in acetone to a concentration of 10 ppm. The solutions were pipetted into the wells of depression slides and allowed to dry. The wells were filled with a suspension of the fungus spores. The spores were then incubated in a moist chamber overnight. A group of 100 spores was examined and the number of spores germinated and not germinated was counted and recorded to show the biological activity in terms of the percent germination inhibition.

Both compounds tested showed 100% germination inhibition.

EXAMPLE 8

Tomato Early Blight 1-tolyl-3-methyl-5-(trichlorovinylimino)-imidazolidine-2,4-dione was tested for the control of the tomato early-blight organism, Alternaria solani condidia. Tomato (v. Bonny Best) seedlings of 6 to 7 weeks old were used. The tomato plants were sprayed with a 100-ppm solution of the test compound in an acetone-and-water solution containing a small amount of a monionic emulsifier. The sprayed plants were inoculated one day later with the organism, dried and maintained at 60–80% relative humidity for about 12 days. Percent disease control was based on the percent disease development on untreated check plants. The test compound gave 86% disease control.

EXAMPLE 9

Celery Late Blight

The celery late-blight tests were conducted using celery (Utah) plants 11 weeks old. The celery late-blight organism was Septoria apii. The celery plants were sprayed with a 150-ppm solution of the test compound mixed in an acetone-and-water solution containing a small amount of a nonionic emulsifier. The plants were then inoculated with the organism and placed in an environmental chamber and incubated at 66°–68° F. in 100% relative humidity for an extended period of time (approximately 48 hours). Following the incubation the plants were allowed to dry and then were maintained at a 60–80% relative humidity for approximately 14 days. The percent disease control provided by a given test compound is based on the percent disease reduction relative to untreated check plants. The results are reported in Table III.

EXAMPLE 10

Leaf Rust

The leaf-rust test was made using pinto beans. The pathogen was Uronyces phaseoli tipica. The pinto-bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68°–70° F. The plants were then removed from the chamber, allowed to dry, and then maintained in a greenhouse at a 60–80% relative humidity. The rate of infection on the leaves was made after about 14 days. The percent disease control provided by a given test compound was based on the disease reduction relative to untreated check plants. The results are reported in Table IV.

When used as fungicides, the compounds of the invention are formulated and applied in fungicidal amounts by conventional art methods to fungi or hosts which are subject to fungus attack, especially vegetative hosts such as plants, plant seeds, etc. The amount used will, of course, depend upon several factors such as the host, the type of fungus, the particular imidazolidinedione, etc. The amount used will generally range from 2 to 90% by weight.

The compounds of the invention are generally admixed with biologically inert liquids or solids in an amount from about 0.005 to 95 weight percent. Higher or lower amounts can be used to advantage. Preferably from 1 to 50 weight percent of the composition will be the imidazolidinedione. Typical of the liquid carrier which may be admixed with the imidazolidinediones of this invention include liquids such as acetone, water, kerosene, xylene, alcohols, alkylated naphthylene and glycols. Typical solids which may be incorporated with the imidazolidinediones include the natural clays such as kaolin clays and diatomaceous earth, synthetic fine silica, talc, pyrophyllite, etc.

Fungicidal formulations may also contain stabilizers, spreading agents, sticking agents, fillers, other compatible pesticides, and the like.

TABLE I

| Compound | Melting Point °C. | Elemental Analysis, % Calculated | | | | Found | | | |
|---|---|---|---|---|---|---|---|---|---|
| | | C | H | Cl | N | C | H | Cl | N |
| 1-ethyl-3-phenyl-5-(1-hydroxy-2,2,2-trichloroethylimino)-imidazolidine-2,4-dione | 140–145 | 42.8 | 3.3 | 29.2 | 11.5 | 43.9 | 3.9 | 29.3 | 11.8 |
| 1-phenyl-3-methyl-5-(1,2,2,2-tetrachloroethylimino)-imidazolidine-2,4-dione | 147–151 | 39.1 | 2.5 | 38.4 | 11.3 | 40.6 | 2.6 | 36.0 | 11.7 |
| 1-(2-fluorophenyl)-3-methyl-5-(1,2,2-trichloro-2-bromoethylimino)-imidazolidine-2,4-dione | 157–160 | — | — | 9.26* | — | — | — | 9.0* | — |
| 1-(3,4-dichlorophenyl)-3-methyl-5-(1,2,2,2-tetrachloroethylimino)-imidazolidine-2,4-dione | 178–180 | 32.9 | 1.6 | 48.6 | 9.6 | 32.5 | 1.4 | 48.3 | 11.5 |
| 1-(2-fluorophenyl)-2-methyl-5-(trichlorovinylimino)-imidazolidine-2,4-dione | oil | 41.1 | 2.0 | 30.3 | 12.0 | 43.2 | 2.5 | 27.8 | 11.5 |
| 1-(3-chlorophenyl)-3-methyl-5-(trichlorovinylimino)-imidazolidine-2,4-dione | oil 39.3 | 1.9 | 38.6 | 11.5 | 40.2 | 1.8 | 40.5 | 11.2 | |
| 1-(phenyl)-3-methyl-5-(trichlorovinylimino)-imidazolidine-2,4-dione | 112–115 | 43.3 | 2.4 | 32.0 | 12.6 | 45.5 | 2.5 | 29.8 | 12.7 |
| 1-methyl-3-phenyl-5-(trichlorovinylimino)-imidazolidine-2,4-dione | 128–130 | 43.3 | 2.4 | 32.0 | 12.6 | 43.5 | 2.3 | 31.4 | 13.4 |
| 1-(p-tolyl)-3-methyl-5-(trichlorovinylimino)-imidazolidine-2,4-dione | oil | 45.1 | 2.9 | — | 12.1 | 45.8 | 3.0 | — | 14.0 |
| 1-(3,4-dichlorophenyl)-3-methyl-5-(trichlorovinylimino)-imidazolidine-2,4-dione | oil | 35.9 | 1.5 | — | 10.5 | 36.7 | 2.2 | — | 11.1 |
| 1-ethyl-3-phenyl-5-(trichlorovinylimino)-imidazolidine-2,4-dione | 111–114 | — | — | 30.7 | — | — | — | 29.7 | — |
| 1-methyl-3-(3-chlorophenyl)-5-(trichlorovinylimino)-imidazolidine-2,4-dione | 166–170 | — | — | 38.6 | — | — | — | 36.6 | — |
| 1-methyl-3-(m-tolyl)-5-trichlorovinylimino)-imidazolidine-2,4-dione | 97–100 | — | — | 30.7 | — | — | — | 30.7 | — |
| 1-n-butyl-3-phenyl-5-(trichlorovinylimino)-imidazolidine-2,4-dione | oil | 48.1 | 3.8 | — | 11.2 | 47.0 | 4.2 | — | 12.2 |
| 1-methyl-3-(2-fluorophenyl)-5-(trichlorovinylimino)-imidazolidine-2,4-dione | 119–24 | — | — | 30.3 | — | — | — | 30.2 | — |
| 1-methyl-3-phenyl-5-(1,2,2,2-tetrachloroethylimino)-imidazolidine-2,4-dione | 158–160 | 39.1 | 2.5 | 38.4 | 11.4 | 39.2 | 2.3 | 38.5 | 11.4 |
| 1-(2-fluorophenyl)-3-methyl-5-(1-hydroxy-2,2,2-trichloroethylimino)-imidazolidine-2,4-dione | 119–122 | — | — | 28.9 | — | — | — | 28.8 | — |
| 1-methyl-3-phenyl-5-(1-hydroxy-2,2,2-trichloroethylimino)-imidazolidine-2,4-dione | 185–188 | 41.1 | 2.9 | 11.5 | 30.5 | 41.8 | 3.1 | 12.2 | 28.5 |
| 1-p-tolyl-3-methyl-5-(1-hydroxy-2,2,2-trichloroethylimino)-imidazolidine-2,4-dione | 170–172 | 42.8 | 3.3 | 29.2 | 11.5 | 41.7 | 3.1 | 29.4 | 11.4 |
| 1-(4-methoxyphenyl)-3-methyl-5-(1-hydroxy-2,2,2-trichloroethylimino)-imidazolidine-2,4-dione | 162–165 | 41.0 | 3.2 | 27.9 | 11.0 | 40.3 | 2.9 | 25.8 | 11.4 |
| 1-(4-methoxyphenyl)-3-methyl-5-(1,2,2,2-tetrachloroethylimino)-imidazolidine-2,4-dione | 136–138 | 39.1 | 2.8 | 35.5 | 10.5 | 39.2 | 2.7 | 35.2 | 10.9 |
| 1-α-naphthyl-3-methyl-5-(1-hydroxy-2,2,2-trichloroethylimino)-imidazolidine-2,4-dione | 60–70 | 48.0 | 3.0 | 26.6 | 10.5 | 47.4 | 3.2 | 28.8 | 9.6 |
| 1-allyl-3-methyl-5-(trichlorovinylimino)-imidazolidine-2,4-dione | oil | 36.5 | 2.7 | 35.9 | 14.2 | 35.8 | 2.5 | 35.5 | 13.2 |
| 1-(3,5-dichlorophenyl)-3-methyl-5-(trichlorovinylimino)-imidazolidine-2,4-dione | 115–119 | 35.9 | 1.5 | 44.1 | 10.5 | 37.7 | 2.2 | 39.3 | 10.7 |

*total halogen in milliequivalents/gram

TABLE II

| Compound | Herbicidal Effectiveness | | | | | |
|---|---|---|---|---|---|---|
| | O | W | C | M | P | L |
| 1-phenyl-3-methyl-5-(1-hydroxy-2,2,2-trichloroethylimino)-imidazolidine-2,4-dione | 100 | 100 | 100 | 100 | 100 | 100 |
| 1-(2-fluorophenyl)-3-methyl-5-(1,2,2,2-tetrachloroethylimino)-imidazolidine-2,4-dione | 100 | 100 | 100 | 100 | 100 | 100 |
| 1-ethyl-3-phenyl-5-(1-hydroxy-2,2,2-trichloroethylimino)-imidazolidine-2,4-dione | 70 | 80 | 90 | 85 | 45 | 40 |
| 1-phenyl-3-methyl-5-(1,2,2,2-tetrachloroethylimino)-imidazolidine-2,4-dione | 65 | 50 | 80 | 100 | 90 | 90 |
| 1-(2-fluorophenyl)-3-methyl-5-(1,2,2-trichloro-2-bromoethylimino)-imidazolidine-2,4-dione | 95 | 100 | 100 | 100 | 100 | 100 |
| 1-(3,4-dichlorophenyl)-3-methyl-5-(1,2,2,2-tetrachloroethylimino)-imidazolidine-2,4-dione | 65 | 100 | 100 | 100 | 100 | 100 |
| 1-(2-fluorophenyl)-3-methyl-5-(trichlorovinylimino)-imidazolidine-2,4-dione | 100 | 100 | 100 | 100 | 100 | 100 |

TABLE II-continued

| Compound | Herbicidal Effectiveness | | | | | |
|---|---|---|---|---|---|---|
| | O | W | C | M | P | L |
| 1-(3-chlorophenyl)-3-methyl-5-trichlorovinyl-imino)-imidazolidine-2,4-dione | 60 | 30 | 60 | 95 | 25 | 25 |
| 1-(4-chlorophenyl)-3-methyl-5-(trichlorovinyl-imino)-imidazolidine-2,4-dione | 50 | 70 | 75 | 100 | 95 | 95 |
| 1-methyl-3-phenyl-5-(trichlorovinylimino)-imidazolidine-2,4-dione | 80 | 45 | 90 | 100 | 95 | 90 |
| 1-(3,4-dichlorophenyl)-3-methyl-5-(trichlorovinyl-imino)-imidazolidine-2,4-dione | 30 | 40 | 70 | 100 | 100 | 100 |
| 1-(2-fluorophenyl)-3-methyl-5-(trichlorovinyl-imino)-imidazolidine-2,4-dione | 80 | 35 | 75 | 100 | 100 | 75 |
| 1-ethyl-3-phenyl-5-(trichlorovinyl-imino)-imidazolidine-2,4-dione | 0 | 0 | 10 | 60 | 30 | 20 |
| 1-methyl-3-(2-fluorophenyl)-5-(trichloro-vinylimino)-imidazolidine-2,4-dione | 100 | 100 | 100 | 100 | 100 | 100 |
| 1-methyl-3-phenyl-5-(1,2,2,2-tetrachloro-ethylimino)-imidazolidine-2,4-dione | 100 | 100 | 100 | 100 | 100 | 100 |
| 1-(2-fluorophenyl)-3-methyl-5-(1-hydroxy-2,2,2-trichloroethylimino)-imidazolidine-2,4-dione | 90 | 100 | 100 | 100 | 100 | 100 |
| 1-methyl-3-phenyl-5-(1-hydroxy-2,2,2-trichloroethylimino)-imidazolidine-2,4-dione | 90 | 100 | 100 | 100 | 100 | 100 |
| 1-(4-methoxyphenyl)3-methyl-5-(1-hydroxy-2,2,2-trichloroethylimino)-imidazolidine-2,4-dione | 85 | 65 | 100 | 100 | 95 | 95 |
| 1-(4-methoxyphenyl)-3-methyl-5-(1,2,2,2-tetrachloroethylimino)-imidazolidine-2,4-dione | 65 | 60 | 95 | 100 | 100 | 100 |
| 1-α-naphthyl-3-methyl-5-(1-hydroxy-2,2,2-trichloroethylimino)-imidazolidine-2,4-dione | 45 | 50 | 40 | 10 | 10 | 10 |
| 1-(3,5-dichlorophenyl)-3-methyl-5-(tri-chlorovinylimino)-imidazolidine-2,4-dione | 0 | 0 | 0 | 75 | 80 | 90 |

O = Wild Oats (*Avena fatua*)
W = Watergrass (*Echinochloa Crusgalli*)
C = Crabgrass (*Digitaria Sanguinalis*)
M = Mustard (*Brassica arvensis*)
P = Pigweed (*Amaranthus retroflexus*)
L = Lambsquarter (*Chenopodium album*)

TABLE III

| Compound | % Control |
|---|---|
| 1-allyl-3-methyl-5-(trichlorovinylimino)-imidazolidine-2,4-dione | 37 |
| 1-(m-chlorophenyl)-3-methyl-5-(trichloro-vinylimino)-imidazolidine-2,4-dione | 71 |
| 1-(p-chlorophenyl)-3-methyl-5-(trichloro-vinylimino)-imidazolidine-2,4-dione | 84 |
| 1-methyl-3-phenyl-5-(trichlorovinylimino)-imidazolidine-2,4-dione | 84 |
| 1-p-tolyl-3-methyl-5-(trichlorovinylimino)-imidazolidine-2,4-dione | 81 |
| 1-methyl-3-m-tolyl-5-(trichlorovinylimino)-imidazolidine-2,4-dione | 80 |
| 1-methyl-3-m-chlorophenyl-5-(trichloro-vinylimino)-imidazolidine-2,4-dione | 51 |
| 1-(3,5-dichlorophenyl)-3-methyl-5-(tri-chlorovinyl)-2,4-imidazolidine-2,4-dione | 64 |
| 1-methyl-3-phenyl-5-(1,2,2,2-tetrachloro-ethylimino)-imidazolidine-2,4-dione | 39 |
| 1-o-fluorophenyl-1-methyl-5-(2-bromo-1,2,2-trichloroethylimino)-imidazolidine-2,4-dione | 23 |
| 1-p-tolyl-3-methyl-5-(1-hydroxy-2,2,2-trichloroethylimino)-imidazolidine-2,4-dione | 11 |
| 1-(3,4-dichlorophenyl)-3-methyl-5-(1,2,2,2-tetrachloroethylimino)-imidazolidine-2,4-dione | 50 |

TABLE IV

| Compound | % Control |
|---|---|
| 1-methyl-3-phenyl-5-(1,2,2,2-tetrachloro-ethylimino)-imidazolidine-2,4-dione | 44 |
| 1-o-fluorophenyl-3-methyl-5-(1-hydroxy-2,2,2-trichloroethylimino)-imidazoi-dine-2,4-dione | 23 |
| 1-methyl-3-phenyl-5-(1-hydroxy-2,2,2-tri-chloroethylimino)-imidazolidine-2,4-dione | 37 |
| 1-phenyl-3-methyl-5-(1-hydroxy-2,2,2-tri-chloroethylimino)-imidazolidine-2,4-dione | 39 |
| 1-ethyl-3-phenyl-5-(1,2,2,2-tetrachloro-29 ethylimino)-imidazolidine-2,4-dione | |

What is claimed is:

1. Compound of the formula

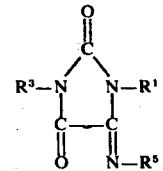

wherein one $R^1$ or $R^3$ group is alkyl of 1 to 6 carbon atoms and the other $R^1$ or $R^3$ group is alkenyl of 3 to 6 carbon atoms or naphthyl; and $R^5$ is 1-hydroxy-2,2,2-trihaloethyl, 1,2,2,2-tetrahaloethyl trihalovinyl or dihalovinyl wherein the halogen is of atomic number 17 to 35.

2. The compound of claim 1 wherein one of $R^1$ or $R^3$ is alkyl and the other of $R^1$ or $R^3$ is alkenyl.

3. The compound of claim 2 wherein $R^5$ is trihalovinyl.

4. The compound of claim 3 wherein $R^5$ is trichlorovinyl.

5. The compound of claim 4 wherein $R^1$ is allyl and $R^3$ is methyl.

6. The compound of claim 1 wherein one of $R^1$ or $R^3$ is alkyl and the other of $R^1$ or $R^3$ is naphthyl.

7. The compound of claim 6 wherein $R^1$ is naphthyl, $R^3$ is methyl and $R^5$ is 1-hydroxy-2,2,2-trichloroethyl.

* * * * *

UNITED STATES PATENT AND TRADEMARK OFFICE
CERTIFICATE OF CORRECTION

PATENT NO. : 3,992,402
DATED : Nov. 16, 1976
INVENTOR(S) : Malcolm S. Singer

It is certified that error appears in the above-identified patent and that said Letters Patent are hereby corrected as shown below:

Columns 9 and 10 of Table I should read:

| Compound | Melting Point °C. | Elemental Analysis, % | | | | | | | |
|---|---|---|---|---|---|---|---|---|---|
| | | Calculated | | | | Found | | | |
| | | C | H | Cl | N | C | H | Cl | N |
| 1-(3-chloropheny)-3-methyl-5-(trichlorovinylimino)-imidazolidine-2,4-dione | oil | 39.3 | 1.9 | 38.6 | 11.5 | 40.2 | 1.8 | 40.5 | 11.2 |

UNITED STATES PATENT OFFICE
CERTIFICATE OF CORRECTION

Patent No. 3,992,402  Dated November 16, 1976

Inventor(s) Malcolm S. Singer  Page 2 of 2

It is certified that error appears in the above-identified patent and that said Letters Patent are hereby corrected as shown below:

Columns 11 and 12 of Table II should read:

| Compound | O | W | C | M | P | L |
|---|---|---|---|---|---|---|
| 1-p-tolyl-3-methyl-5-(1-hydroxy-2,2,2-trichloroethylimino)-imidazolidine-2,4-dione | 95 | 65 | 100 | 100 | 100 | 100 |

Column 12 of Table IV, 5th compound should read:

| Compound | % Control |
|---|---|
| 1-ethyl-3-phenyl-5-(1,2,2,2-tetrachloroethylimino)-imidazolidine-2,4-dione | 29 |

Signed and Sealed this

Seventh Day of June 1977

[SEAL]

Attest:

RUTH C. MASON
Attesting Officer

C. MARSHALL DANN
Commissioner of Patents and Trademarks